US008676511B2

(12) United States Patent
Jeffrey et al.

(10) Patent No.: US 8,676,511 B2
(45) Date of Patent: Mar. 18, 2014

(54) METHOD AND SYSTEM FOR PREDICTING LIVER FIBROSIS AND RELATED PATHOLOGIES

(76) Inventors: Gary Jeffrey, Perth (AU); Enrico Rossi, Nedlands (AU); Mahesh Bulsara, Bull Creek (AU); Leon Adams, Attadale (AU)

( * ) Notice: Subject to any disclaimer, the term of this patent is extended or adjusted under 35 U.S.C. 154(b) by 1909 days.

(21) Appl. No.: 11/388,766

(22) Filed: Mar. 24, 2006

(65) Prior Publication Data

US 2007/0225919 A1 Sep. 27, 2007

(51) Int. Cl.
*G01N 33/48* (2006.01)

(52) U.S. Cl.
USPC .......................................................... 702/19

(58) Field of Classification Search
None
See application file for complete search history.

(56) References Cited

U.S. PATENT DOCUMENTS

| 6,631,330 B1 | 10/2003 | Poynard |
| 6,986,995 B2 | 1/2006 | Rose et al. |
| 2003/0175686 A1 | 9/2003 | Rose et al. |
| 2004/0039553 A1 | 2/2004 | Poynard |
| 2005/0186561 A1 | 8/2005 | Oh et al. |
| 2007/0225919 A1 | 9/2007 | Jeffrey et al. |

FOREIGN PATENT DOCUMENTS

DE 198 36 651 2/2000

OTHER PUBLICATIONS

Hui et al., The American Journal of Gastroenterology, 2005, vol. 100, Issue 3, pp. 616-623; Published Online: Mar. 2, 2005.*
Marcellin et al., Hepatology, 2002, p. S47-S56.*
Adams et al., Hepascore: An accurate Validated Predictor of Liver Fibrosis in Chronic Hepatitis C Infection, Clinical Chemistry: 51: 10, 1867-1873, 2005.
Anderson, SP et al., Delayed Liver Regeneration in Peroxisome Proliferator-Activated Receptor-α-Null Mice, Hepatology 36:544-554, (2002).
Booth et al., Clinical guidelines on the Management of Hepatitis C, Gut 49:I1-21(2001).
Brandt et al., A Convenient Radiometric Assay for Hyaluronan, Acta Otolaryn. 442 (Suppl.): 31-35 (1987).
Bravo et al., Liver Biopsy, N Engl J Med 344:495-500 (2001).
Chichibu et al., Assay of Serum Hyaluronic Acid in Clinical Application, Clin. Chim. Acta 181:317-324 (1989).
Delpech et al., Immunoenzymoassay of the Hyaluronic Acid-Hyaluronectin Interaction: Application to the Detection of Hyaluronic Acid in Serum of Normal Subjects and Cancer Patients, Anal. Biochem. 149:555-565 (1985).
EASL International Consensus Conference on Hepatitis C, J Hepatol 31 (Supp. 1):3-8 (1999).
Engstrom-Laurent et al., Concentration of Sodium Hyaluronate in Serum, Scand. J. Clin. Lab. Invest. 45:497-504 (1985).
Fried et al., Peginterferon Alfa-2α Plus Ribavirin for Chronic Hepatitis C Virus Infection, N Engl J Med 347:975-82 (2002).
Giannini et al., Validity and Clinical Utility of the Aspartate Aminotransferase-Alanine Aminotransferase Ratio in Assession Disease Severity and Prognosis in Patients With Hepatitis C Virus-Related Chronic Liver Disease, Arch Intern Med 163:218-24 (2003).
Gilmore et al., Indications, Methods and Outcomes of Percutaneous Liver Biopsy in England and Wales: an audit by the British Society of Gastroenterology and the Royal College of Physicians of London, Gut 36:437-419 (1995).
Goldberg, Enzyme-Linked Immunosorbent Assay for Hyaluronate Using Cartilage Proteoglycan and an Antibody to Keratan Surfate, Anal. Biochem. 174:448-458 (1988).
Hall and Roberts, Physical and Chemical Properties of Human Plasma $\alpha_2$-Macroglobulin, Biochem. J. 171:27-38, (1978).
Imbert-Bismut et al., Biochemical Markers of Liver Fibrosis in Patients With hepatitis C Virus Infection: a Prospective Study, Lancet 357: 1069-75 (2001).
Inber and Pizzo, Clearance and Binding of Two Electrophoretic "Fast" Forms of Human $\alpha_2$-Macroglobulin, Journal of Biological Chemistry, 256(15): 8134-8139, (1981).
Kasahara et al., Circulating Matrix Metalloproteinase-2 and Tissue Inhibitor of Metalloproteinase-1 as Serum Markers of Fibrosis in Patients with Chronic Hepatitis C, J Hepatol 26:574-83 (1997).
Kim et al., Cancer-Associated Molecular Signature in the Tissue Samples of Patients With Cirrhosis, Hepatology 38: 518-26 (2003).
Kim, The Burden of Hepatitis C in the United States, Hepatology 36:S30-42 (2002).
Kleiner et al., Design and Validation of a Histological Scoring System for Nonalcoholic Fatty Liver Disease, Hepatology 41: 1313 (2005).
Laurent and Tengblad, Determination of Hyaluronate in Biological Samples by a Specific Radioassay Technique, Anal. Biochem. 109:386-394 (1980).
Li et al., Accumulatin of Hyaluronate in Human Lung Carcinoma as Measured by a New Hyaluronate Elisa, Conn. Tissue Res. 19:243-254 (1989).

(Continued)

*Primary Examiner* — Pablo S Whaley
(74) *Attorney, Agent, or Firm* — Foley & Lardner LLP

(57) ABSTRACT

Provided herein are methods of detecting and staging liver fibrosis in an individual with liver disease. Also provided are methods of detecting necroinflammatory activity. Invention methods utilize four serum markers, age, and gender to determine an end value. The end value is compared to a cut-off value, in order to identify significant fibrosis (METAVIR stages F2 to F4), or an absence of advanced fibrosis (stages F3 and F4) or cirrhosis (stage F4). In particular aspects, progression or treatment of liver fibrosis can be monitored by invention methods. The end value is also used to distinguish between no to mild necroinflammatory activity (METAVIR grade A0 to A1) and moderate to severe necroinflammatory activity (grade A2 to A3).

34 Claims, 5 Drawing Sheets

(56) References Cited

OTHER PUBLICATIONS

Lindquist et al., Seven Different Assays of Hyaluronan Compared for Clinical Utility, Clin. Chem. 38:127-132 (1992).

McHutchinson, John J. et al., Measurement of Serum Hyaluronic Acid in Patients with Chronic Hepatitis C and its Relationship to liver Histology, J. Gastroenterol Hepatol 15:945-51, (2000).

Meyers et al., Serum biochemical markers accurately predict liver fibrosis in HIV and hepatitis C virus co-infected patients. AIDS 17:521-525, (2003).

Poole et al., Inflammation and Cartilage Metabolism in Rheumatoid Arthritis, J. Biol. Chem. 260:6020-6025 (1985).

Poole et al., Rabbit Antibodies to Degraded and Intact Glycosaminoglycans Which Are Naturally Occurring and Present in Arthritic Rabbits, Arth. Rheum. 33:790-799 (1990).

Poynard et al., Biochemical markers of liver fibrosis in patients infected by hepatitis C virus: longitudinal validation in a randomized trial. Journal of Hepat. 9:128-133, (2002).

Poynard et al., Natural History of Liver Fibrosis Progression in Patients With Chronic Hepatitis C, Lancet 349: 825-32 (1997).

Regev et al., Sampling Error and Intraobserved Variation in Liver Biopsy in Patients With Chronic HCV Infection, Am J Gastroenterol 97:2614-8 (2002).

Rossi et al., Validation of the Fibro Test Biochemical Markers Score in Assessing Liver Fibrosis in Hepatitis C Patients, Clin Chem 49: 450-454 (2003).

Strader et al., Diagnosis, Management, and Treatment of Hepatitis C, Hepatology 39: 1147-71 (2004 ).

Sud et al., Improved Prediction of Fibrosis in Chronic Hepatitis C Using Measures of Insulin Resistance in a Probability Index, Hepatology 39:1239-47 (2004 ).

The Nomenclature of Lipids, Biochem. J. 171:221-35, (1978).

Becker, et al, Validation of Hepascore, Compared with Simple Indices of Fibrosis, in Patients with Chronic Hepatitis C Virus Infection in United States, Clin Gastroenter Hepatol, (2009), 7:696-701.

International Search Report dated Dec. 20, 2010 in PCT application PCT/US2010/053434.

Patella, et al, Follistatin attenuates early liver fibrosis: effect on hepatic stellate cell activation and hepatocyte apoptosis, Am J Physiol Gastrointest Liver Physiol, (2006), 290:G137-G144.

Office Action dated Oct. 11, 2011 for U.S. Appl. No. 12/616,096.

Armstrong et al., "$\alpha_2$-macroglobulin: an evolutionarily conserved arm of the innate immune system," Developmental and Comparative Immunology, vol. 23, pp. 375-390, 1999.

Office Action issued on Jul. 16, 2012 by the Examiner in U.S. Appl. No. 12/616,096.

\* cited by examiner

METHOD AND SYSTEM FOR PREDICTING LIVER FIBROSIS AND RELATED PATHOLOGIES

FIELD OF THE INVENTION

The present invention relates generally to the field of medical diagnostics, in particular, diagnosis and staging of hepatic fibrosis.

BACKGROUND OF THE INVENTION

Liver fibrosis is a gradual process of increased production and decreased degradation of extracellular matrix materials. It is generally viewed that damage to hepatic cells initiates the process of fibrosis formation through activation and secretion of multiple cellular factors from Kupffer cells (macrophages which line the liver sinusoids). Such factors, in addition to factors secreted by damaged hepatocytes, thrombocytes, and endothelial cells of the hepatic sinusoid and other mediators, activate hepatic stellate cells. Activated hepatic stellate cells differentiate into myofibroblasts, which proliferate and synthesize a massive amount of extracellular materials that gradually accumulate, resulting in the development of liver fibrosis.

Liver fibrosis is common to liver diseases of many etiologies, including chronic viral hepatitis B and C, autoimmune liver disease, such as autoimmune hepatitis and primary biliary cirrhosis, alcoholic liver disease, nonalcoholic fatty liver disease, metabolic disorders, such as lipid, glycogen, or metal storage disorders, and drug-induced liver disease. The fibrosis exhibited in these disorders results from chronic insults to the liver from, for example, viral infection, alcohol, or drugs.

Hepatitis C, for example, is one of the leading causes of chronic liver disease in the United States, where an estimated 3.9 million people are chronically infected with hepatitis C virus (HCV) and approximately 30,000 new cases of acute HCV occur each year. Thus, the prevalence of hepatitis C is estimated to be 1.8% in the United States, with as many as 10,000 deaths per year resulting from chronic HCV infection (Alter, Semin. Liver Dis. 15:5-14 (1995)). World-wide, the prevalence of chronic HCV infection is estimated to be about 3% (J Viral Hepat 6:35-47 (1999)). Moreover, death, hospitalization and liver transplantation as a result of chronic hepatitis C have increased significantly in the past decade (Hepatology 36:S30-42 (2002)). Liver fibrosis is the main determinant of hepatitis C virus related morbidity and mortality (Lancet 349:825-323 (1997)). Furthermore, the stage of fibrosis is prognostic and provides information on the likelihood of disease progression and response to treatment (Hepatology 36:S47-564, 5 (2002); N Engl J Med 347:975-82 (2002)). The presence of significant fibrosis (equivalent to METAVIR F2 or greater) as determined by liver biopsy, is widely accepted as an indication to commence treatment (Gut 49:11-21 (2001); J Hepatol 31:3-8 (1999); Hepatology 39:1147-71 (2004)). The presence of cirrhosis has implications regarding screening for hepatocellular carcinoma and esophageal varices (J Hepatol 31:3-8 (1999)).

Liver biopsy is currently the gold standard for staging fibrosis, but has well documented complications including pain, bleeding and, rarely, death (Gut 36:437-419, (1995); N Engl J Med 344:495-500 (2001)). Liver biopsy is also expensive, as are the costs associated with treating any resulting complications. In addition, inter- and intra-observer error may lead to incorrect staging (Hepatology 36:S47-564, 5 (2002)), as may sampling error in up to 33% of biopsies (Am J Gastroenterol 97:2614-8 (2002)).

Routinely measured serum markers, used either individually or in combination, have been examined as alternatives to liver biopsy for staging fibrosis among hepatitis C patients. Platelet count, ratio of aspartate aminotransferase (AST) to alanine aminotransferase (ALT), or a combination of AST and platelet count, are reliable predictors of cirrhosis (Arch Intern Med 163:218-24 (2003)). However, their predictive value for mild or moderate fibrosis is insufficient to be of clinical utility (Hepatology 38: 518-26 (2003); Hepatology 39: 1456-7 (2004)). More complex models which include routinely available analytes such as cholesterol, γ-glutamyltransferase (GGT), platelet count, and prothrombin time, have a high negative predictive value (NPV) for excluding significant hepatic fibrosis, but have poor positive predictive value (PPV) and are only applicable to approximately one third of patients (Hepatology 39:1456-7 (2004)). A recently reported model incorporating measures of insulin resistance and past alcohol intake, reliably predicted significant fibrosis, but was less accurate in excluding significant fibrosis (Hepatology 39:1239-47 (2004)).

In efforts to improve the accuracy of noninvasive methods of staging liver fibrosis, several non-routinely-available biochemical markers associated with collagen and extra-cellular matrix deposition/degradation have been examined. Serum levels of hyaluronic acid, tissue inhibitor of matrix metalloproteinase-1 (TIMP-1) and matrix metalloproteinase-2 (MMP-2) correlate with liver fibrosis, but by themselves have low predictive value for diagnosing significant fibrosis (J Gastroenterol Hepatol 15:945-51, 18 (2000); J Hepatol 26:574-83 (1997)). "FibroTest" (BioPredictive S.A.S., Paris, France), which combines multiple biochemical markers with age and gender, was accurate in detecting significant fibrosis in just under half of patients from a center in France (Lancet 357: 1069-75 (2001)). However, when applied to a population of hepatitis C patients from our institution, FibroTest was less accurate and had a PPV of less than 80%. (Clin Chem 49: 450-420 (2003))

SUMMARY OF THE INVENTION

Provided herein are methods of diagnosing the presence and extent of liver fibrosis in a patient. The method is accomplished by determining a score based on age, gender, and the concentrations in serum of α2-macroglobulin, γ-glutamyl transferase (GGT), bilirubin, and hyaluronic acid (HA).

Provided herein are methods of differentiating between degrees of liver fibrosis; in particular, predicting the presence of significant fibrosis and predicting the absence of advanced liver fibrosis in an individual. This method is accomplished by obtaining a sample from the individual and determining the levels of four markers, $\alpha_2$-macroglobulin (α2MG), hyaluronic acid (HA), bilirubin, γ-glutamyl transferase (GGT). The levels of these markers are input into a first equation, along with age and gender to determine an intermediate value. The intermediate value is input into a second equation to determine the end value or Hepascore. The end value is compared to a cut-off value of about 0.5 (preferably 0.5), wherein the individual is diagnosed as having significant liver fibrosis when the Hepascore is greater than or equal to the cut-off value of about 0.5 (preferably 0.5). The individual is diagnosed with no advanced fibrosis if the Hepascore is less than a cut-off value of about 0.5 (preferably 0.5).

Fibrosis is scored on the 5-point METAVIR scale as follows: F0—no fibrosis, F1—portal fibrosis alone, F2—portal fibrosis with rare septae, F3—portal fibrosis with many septae, F4—cirrhosis. "Significant fibrosis" corresponds to stages F2, F3, and F4, while "advanced fibrosis" corresponds to stages F3 and F4.

The phrase "intermediate value" as used herein represents a value, y, calculated from the levels of the four markers, age, and gender using the following equation:

$$y = \exp(-4.185818 - (0.0249 * \text{age}) + (0.7464 * \text{gender}) + (1.0039 * \alpha_2\text{-macroglobulin}) + (0.0302 * \text{hyaluronic acid}) + (0.0691 * \text{bilirubin}) - (0.0012 * \text{GGT}))$$

wherein, age is provided in years; male gender=1, female gender=0, $\alpha_2$-macroglobulin as reported in g/L; hyaluronic acid as reported in µg/L; bilirubin as reported in µmol/L; and GGT as reported in U/L.

The term "coefficient" as used herein refers to the factors that each variable (i.e., age, gender, $\alpha_2$-macroglobulin, hyaluronic acid, bilirubin, and GGT) is multiplied by in the above equation.

The numerical definitions of the constant and the coefficients in the above equation can be varied and still produce a valid intermediate value. For example, the constant, −4.185818, may vary from about −6.846 to about −1.5257; the age coefficient may vary from about −0.0877 to about 0.0378; the gender coefficient may vary from about −0.3064 to about 1.7992; the $\alpha_2$-macroglobulin coefficient can vary from about 0.4406 to about 1.5672; the hyaluronic acid coefficient can vary from about 0.0090 to about 0.0515; the bilirubin coefficient can vary from about −0.0099 to about 0.1482; and the GGT coefficient can vary from about −0.0055 to about 0.0032.

One of skill in the art would recognize that the concentrations of the markers could be provided in units other than the ones recited above. In this case, one would generate an equivalent equation to determine the intermediate value by converting the units as recited above to other units using a mathematical function. The inverse of that function would be performed on the coefficient for that marker. For example, $\alpha_2$-macroglobulin is reported in g/L. If this marker were reported in mol/L (i.e., (g/L)/(molecular weight of $\alpha_2$-macroglobulin)), one would multiply the coefficient for $\alpha_2$-macroglobulin (i.e., 1.0039) by the molecular weight of $\alpha_2$-macroglobulin. One of skill in the art would recognize that in a case in which there is more than one molecular weight for a given marker, one particular molecular weight must be selected and used for both of the above described mathematical functions. The new coefficient would be used in the equation.

The phrases "end value" and "Hepascore" are used interchangeably herein. The Hepascore, H, is a number calculated from the intermediate value using the equation below and ranges from 0.0 to 1.0.

$$H = y/(1+y)$$

The Hepascore is compared with a cut-off value in order to determine the extent of fibrosis. In a particular aspect, a Hepascore greater than or equal to a cut-off value of about 0.5 (preferably 0.5) is predictive of significant fibrosis, or stage F2-F4. A Hepascore less than a cut-off value of about 0.5 (preferably 0.5) is predictive of the absence of advanced fibrosis (stages F3 and F4). A Hepascore less than a cut-off value of about 0.84 (preferably 0.84) is predictive of the absence of cirrhosis (stage F4).

In another aspect, a Hepascore is used as a positive predictor of cirrhosis. In this aspect, a Hepascore greater than or equal to a cut-off value of about 0.84 (preferably 0.84) is indicative of the presence of cirrhosis.

The phrase "cut-off value" as used herein refers to a Hepascore value that is statistically predictive of a symptom or disease or lack thereof. In a particular aspect, the cut-off value is about 0.5 and the Hepascore distinguishes between significant fibrosis and an absence of advanced fibrosis. For example, a Hepascore greater than or equal to a cut-off value of about 0.5 is predictive of significant fibrosis. A Hepascore less than a cut-off value of about 0.5 is predictive of an absence of advanced fibrosis. In certain embodiments, this cut-off value may be between 0.425 to 0.575 inclusive, or between 0.450 to 0.550 inclusive, or between 0.475 to 0.525 inclusive. Alternatively, the cut-off value may be 0.425, 0.450, 0.5 0.475, 0.525, 0.550, and even 0.575. The above numbers are subject to 5% variation.

In another aspect, the cut-off value is about 0.84, more preferably 0.84 and the Hepascore can distinguish between the presence or absence of cirrhosis. For example, a Hepascore greater than or equal to about 0.84 (preferably 0.84) is predictive of cirrhosis. In certain embodiments, this cut-off value may be between 0.70 to 0.95 inclusive, or between 0.75 to 0.90 inclusive, or between 0.80 to 0.85 inclusive. Alternatively, the cut-off value may be 0.95, 0.90, 0.84, 0.80, 0.75, and even 0.70. The above numbers are subject to 5% variation.

The term "about" as used herein in reference to numbers or quantitative measurements, refers to the indicated value plus or minus 10%.

Also provided herein are methods of monitoring progression of liver fibrosis in a patient suffering from a liver disease. This method is accomplished by obtaining a first sample from the individual and a second sample from the same individual, at a time after the first sample. The levels of four markers, $\alpha_2$-macroglobulin ($\alpha$2MG), hyaluronic acid (HA), bilirubin, $\gamma$-glutamyl transferase (GGT) are determined in each sample. These levels are input into a first equation, along with age and gender, to determine an intermediate value corresponding to each sample. The intermediate value is input into a second equation to determine the an end value or Hepascore, corresponding to each sample. The end values are compared to a cut-off value to determine the extent of liver fibrosis. A Hepascore greater than or equal to a cut-off value of about 0.5 is predictive of significant fibrosis. A Hepascore less than a cut-off value of about 0.5 (preferably 0.5) is predictive of an absence of advanced fibrosis. In certain embodiments, this cut-off value may be between 0.425 to 0.575 inclusive, or between 0.450 to 0.550 inclusive, or between 0.475 to 0.525 inclusive. Alternatively, this cut-off value may be 0.425, 0.450, 0.475, 0.5, 0.525, 0.550, and even 0.575. The above numbers are subject to 5% variation. A Hepascore greater than or equal to about 0.84 is indicative of cirrhosis, whereas a Hepascore less than about 0.84 is indicative of an absence of cirrhosis. In certain embodiments, this cut-off value may be between 0.70 to 0.95 inclusive, or between 0.75 to 0.90 inclusive, or between 0.80 to 0.85 inclusive. Alternatively, this cut-off value may be 0.95, 0.90, 0.84, 0.80, 0.75, and even 0.70. The above numbers are subject to 5% variation. The extent of liver fibrosis (e.g., significant fibrosis, cirrhosis, or an absence of advanced fibrosis) as indicated by the first sample is compared to the extent of liver fibrosis indicated by the second sample; wherein an increase in the extent of liver fibrosis in the second sample as compared with the first indicates progression of liver fibrosis, whereas a decrease in the extent of liver fibrosis in the second sample as compared to the first indicates a regression of liver fibrosis.

Further provided herein are methods of monitoring the efficacy a liver fibrosis therapy in a patient suffering from a liver disease. This method is accomplished by obtaining a first sample from the individual and a second sample from the same individual, at a time after the first sample. The levels of four markers, α-macroglobulin (α2MG), hyaluronic acid (HA), bilirubin, γ-glutamyl transferase (GGT) are determined in each sample. These levels are input into a first equation, along with age and gender, to determine an intermediate value corresponding to each sample. The intermediate value is input into a second equation to determine an end value or Hepascore, corresponding to each sample. The end values are compared to a cut-off value to determine the extent of liver fibrosis. A Hepascore greater than or equal to a cut-off value of about 0.5 (preferably 0.5) is predictive of significant fibrosis. A Hepascore less than a cut-off value of about 0.5 (preferably 0.5) is predictive of an absence of advanced fibrosis. In certain embodiments, this cut-off value may be between 0.425 to 0.575 inclusive, or between 0.450 to 0.550 inclusive, or between 0.475 to 0.525 inclusive. Alternatively, this cut-off value may be 0.425, 0.450, 0.475, 0.5, 0.525, 0.550, and even 0.575. The above numbers are subject to 5% variation. A Hepascore greater than or equal to about 0.84 is indicative of cirrhosis, whereas a Hepascore less than about 0.84 is indicative of an absence of cirrhosis. In certain embodiments, this cut-off value may be between 0.70 to 0.95 inclusive, or between 0.75 to 0.90 inclusive, or between 0.80 to 0.85 inclusive. Alternatively, this cut-off value may be 0.95, 0.90, 0.84, 0.80, 0.75, and even 0.70. The above numbers are subject to 5% variation. The extent of liver fibrosis (e.g., significant fibrosis, cirrhosis, or an absence of advanced fibrosis) as indicated by the first sample is compared to the extent of liver fibrosis indicated by the second sample; wherein either no change or an increase in the extent of liver fibrosis in the second sample as compared with the first indicates the liver fibrosis therapy is not efficacious, whereas a decrease in the extent of liver fibrosis in the second sample as compared to the first indicates the liver fibrosis therapy is efficacious.

One of skill in the art would recognize that in monitoring liver fibrosis therapy, one could compare samples taken before treatment is initiated to those samples taken after therapy is concluded. One could also compare two samples taken at different times during treatment. One could also compare a sample taken during treatment with one taken after therapy is concluded.

The term "therapy" as used herein refers to any manner of treatment of a disease or symptoms thereof. Therapy of liver fibrosis includes any accepted or experimental treatment. Therapy may include treatment or removal of the causal agent or treatment of the fibrosis with drug compounds or other therapeutic agents.

The terms "efficacy" or "efficacious" as used herein refers to the ability of a drug, therapy or treatment to relieve symptoms or eliminate the disease. A treatment is said to have efficacy if certain positive outcomes, for example, a regression of extent of liver fibrosis, occur as a result of the treatment.

Invention methods may be used for a patient suffering from any disease involving liver fibrosis. In particular, the method of the invention can be performed for detecting liver fibrosis in patients suffering from, for example, hepatitis B, hepatitis C, alcoholism and alcohol abuse, alcoholic liver disease, hemochromatosis, metabolic disease, diabetes, obesity, autoimmune hepatitis, nonalcoholic fatty liver disease, alcoholic fatty liver, drug-induced liver disease, primary biliary cirrhosis, primary sclerosing cholangitis, α1-antitrypsin deficiency, Wilson disease, and chronic rejection or recurrent liver disease following liver transplantation.

In a particular aspect, are used to evaluate patients infected with chronic viral hepatitis infection (e.g., hepatitis B or C virus), in particular, the hepatitis C virus. In yet another embodiment, the individual is co-infected with at least two viruses, including, for example, one or more of the following: hepatitis B, hepatitis C, hepatitis D and HIV-1.

Alcoholic liver disease consists of a spectrum of diseases from alcoholic fatty liver (i.e., steatosis), to alcoholic hepatitis to cirrhosis. Each of these conditions are pathologically distinct and any or all of these three conditions can occur together in the same patient. Alcoholic fatty liver is characterized by an accumulation of fat within the hepatocytes as a result of alcohol abuse. Fatty liver can be accompanied by inflammation (i.e., steatohepatitis), which can lead to scarring of the liver and cirrhosis. Alcoholic hepatitis may occur separately or in combination with cirrhosis, with a range of severity. This condition is characterized by liver cell necrosis and an inflammatory reaction. Histologically, alcoholic hepatitis is characterized by hepatocytes that are swollen as a result of an increase in intracellular water secondary to increase in cytosolic proteins. Steatosis, often of the macrovesicular type, is present. Cirrhosis is the most severe form of liver disease and occurs when damaged cells are replaced by connective tissue, resulting in scarring of the liver, and eventually liver failure.

Nonalcoholic fatty liver disease (NAFLD) is a condition that occurs predominately in subjects who are overweight or have glucose intolerance and do not use excessive amounts of alcohol. NAFLD refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the hepatocytes. In NASH, the fat accumulation is associated with varying degrees of inflammation (hepatitis) and scarring (fibrosis) of the liver. The term "nonalcoholic" is used because NAFLD and NASH occur in individuals who do not consume excessive amounts of alcohol, however, liver biopsy samples are histologically similar to liver biopsies from patients having liver disease as a result of an excessive intake of alcohol.

In a particular aspect, invention methods are used to evaluate patients diagnosed with or suspected of having fatty liver disease as a result of alcohol abuse or nonoalcoholic fatty liver disease.

The patient population to which the invention pertains is preferably patients receiving tertiary care such as in a tertiary care setting, although patients receiving primary and secondary care also can be evaluated using the invention methods. As used herein the term "primary care facility" means a facility that offers first-contact health care only. As used herein the term "secondary care" refers to services provided by medical specialists who generally do not have first contact with patients (e.g., cardiologist, urologists, dermatologists) such typically occurs in a local (or community) hospitals setting. As used herein, the term "tertiary care facility" means a facility that receives referrals from both primary and secondary care levels and usually offers tests, treatments, and procedures that are not available elsewhere. Thus, in a preferred embodiment, the individual to be tested is receiving tertiary medical care. In further embodiments, the individual to be tested is receiving primary or secondary medical care.

The patient population to which the invention pertains is preferably patients receiving tertiary care such as in a tertiary care setting, although patients receiving primary and secondary care also can be evaluated using the invention methods. As used herein the term "primary care facility means a facility that offers first-contact health care only. As used herein the term "secondary care refers to services provided by medical specialists who generally do not have first contact with patients (eg, cardiologist, urologists, dermatologists) such typically occurs in a local (or community) hospitals setting. As used herein, the term "tertiary care facility means a facility that receives referrals from both primary and secondary care levels and usually offers tests, treatments, and procedures that are not available elsewhere. Thus, in a preferred embodiment, the individual to be tested is receiving tertiary medical care.

The term "disease" as used herein refers to an interruption, cessation, or disorder of body functions, systems, or organs and is characterized usually by a recognized etiologic agent(s), an identifiable group of signs and symptoms, or consistent anatomical alterations.

The term "symptom" as used herein refers to an indication or sign that a person has a disease and include changes from normal anatomical structure or bodily function.

Provided herein are methods of differentiating between degrees of necroinflammatory activity; in particular, distinguishing between no to mild activity and moderate to severe activity. This method is accomplished by obtaining a sample of serum from the individual and determining the levels of four markers, $\alpha_2$-macroglobulin ($\alpha$2MG), hyaluronic acid (HA), bilirubin, $\gamma$-glutamyl transferase (GGT). The levels of these markers are input into a first equation, along with age and gender to determine an intermediate value (y) wherein, $$y=\exp(-4.185818-(0.0249*age)+(0.7464*gender)+(1.0039*\alpha 12\text{-macroglobulin})+(0.0302*\text{hyaluronic acid})+(0.0691*\text{bilirubin})-(0.0012*GGT))$$

and wherein, age is provided in years; male gender=1, female gender=0, $\alpha_2$-macroglobulin as reported in g/L; hyaluronate as reported in µg/L; bilirubin as reported in µmol/L; and GGT as reported in U/L. The intermediate value, y, is input into a second equation to determine the end value or Hepascore (H) wherein, $$H+y/(1+y)$$

A Hepascore greater than or equal to a cut-off value of about 0.5 is predictive of moderate to severe necroinflammatory activity. A Hepascore less than a cut-off value of about 0.5 (preferably 0.5) is predictive of no activity to mild necroinflammatory activity. In certain embodiments, this cut-off value may be between 0.425 to 0.575 inclusive, or between 0.450 to 0.550 inclusive, or between 0.475 to 0.525 inclusive. Alternatively, this cut-off value may be 0.425, 0.450, 0.475, 0.5, 0.525, 0.550, and even 0.575. The above numbers are subject to 5% variation.

Necroinflammatory activity is based upon an assessment of piecemeal and lobular necrosis and can be graded on a four-point METAVIR scale as follows: A0—no activity, A1—mild activity, A2—moderate activity, A3—severe activity.

As used herein the terms "level" or "concentration" of a marker are used interchangeably and refer to the relative or absolute amount or activity of the marker per unit volume by any direct or indirect measurement. One of skill in the art would recognize that any assay useful for determining the level of a marker may be used in invention methods, provided such methods produce a level comparable to that obtained with the preferred methods described herein.

In another aspect, provided herein is a system for diagnosing the presence of liver fibrosis in an individual. This system comprises an input device in data communication with a processor, which is in data communication with an output device.

The input device is used for entry of data including levels of $\alpha_2$-macroglobulin, hyaluronic acid, bilirubin, and $\gamma$-glutamyl transferase as determined from a sample from the individual, and data for age and gender. Data may be entered manually by an operator of the system using a keyboard or keypad. Alternatively, data may be entered electronically, when the input device is a cable in data communication with a computer, a network, a server, or analytical instrument.

The processor comprises software for computing an end value or Hepascore, H, and using the end value to diagnose liver fibrosis. The processor computes the Hepascore, H, using an algorithm, wherein the algorithm is $$H=y/(1+y)$$

wherein, $$y=\exp(-4.185818-(0.0249*age)+(0.7464*gender)+(1.0039*\alpha 2\text{-macroglobulin})+(0.0302*\text{hyaluronic acid})+(0.0691*\text{bilirubin})-(0.0012*GGT))$$

wherein,
age is in years,
male gender=1, female gender=0,
$\alpha_2$-macroglobulin is in g/L,
hyaluronic acid is in µg/L,
bilirubin is in µmol/L, and
GGT is in U/L.

The processor further compares the end value or Hepascore to a cutoff value to diagnose the presence of liver fibrosis, wherein a Hepascore greater than or equal to a cut-off value of about 0.5 is predictive of significant fibrosis. A Hepascore less than a cut-off value of about 0.5 (preferably 0.5) is predictive of an absence of advanced fibrosis. In certain embodiments, this cut-off value may be between 0.425 to 0.575 inclusive, or between 0.450 to 0.550 inclusive, or between 0.475 to 0.525 inclusive. Alternatively, this cut-off value may be 0.425, 0.450, 0.475, 0.5, 0.525, 0.550, and even 0.575. The above numbers are subject to 5% variation. A Hepascore greater than or equal to about 0.84 is indicative of cirrhosis, whereas a Hepascore less than about 0.84 is indicative of an absence of cirrhosis. In certain embodiments, this cut-off value may be between 0.70 to 0.95 inclusive, or between 0.75 to 0.90 inclusive, or between 0.80 to 0.85 inclusive. Alternatively, this cut-off value may be 0.95, 0.90, 0.84, 0.80, 0.75, and even 0.70. The above numbers are subject to 5% variation.

The data output device, in data communication with the processor, receives the diagnosis from the processor and provides the diagnosis to the system operator. The output device can consist of, for example, a video display monitor or a printer.

As used herein, the term "specificity" means the probability that a diagnostic method of the invention gives a negative result when the sample is not positive, for example, of significant fibrosis (i.e., stage F2–F4). Specificity is calculated as the number of true negative results divided by the sum of the true negatives and false positives. Specificity is essentially a measure of how well a method excludes those who do not have a disease or symptom (e.g., significant fibrosis).

The term "sensitivity," as used herein, refers to the characteristic of a diagnostic test that measures the ability of a test to detect a disease (or symptom) when it is truly present. Thus, sensitivity is the proportion of all diseased patients for whom there is a positive test, and is determined as the number of true positives divided by the sum of true positives and false negatives.

The phrase "negative predictive value," as used herein, is synonymous with "NPV" and means the probability that an individual diagnosed as not having fibrosis actually does not have the disease. Negative predictive value can be calculated as the number of true negatives divided by the sum of the true negatives and false negatives. Negative predictive value is determined by the characteristics of the diagnostic method as well as the prevalence of fibrosis in the population analyzed.

The phrase "positive predictive value," as used herein, is synonymous with "PPV" and means the probability that an individual diagnosed as having fibrosis actually has the disease or symptom. Positive predictive value can be calculated as the number of true positives divided by the sum of the true positives and false positives. Positive predictive value is determined by the characteristics of the diagnostic method as well as the prevalence of fibrosis in the population analyzed.

As used herein, the term "accuracy" means the overall agreement between the diagnostic method and the disease state. Accuracy is calculated as the sum of the true positives and true negatives divided by the total number of sample results and is affected by the prevalence of fibrosis in the population analyzed.

DETAILED DESCRIPTION OF THE INVENTION

Figure 1A:
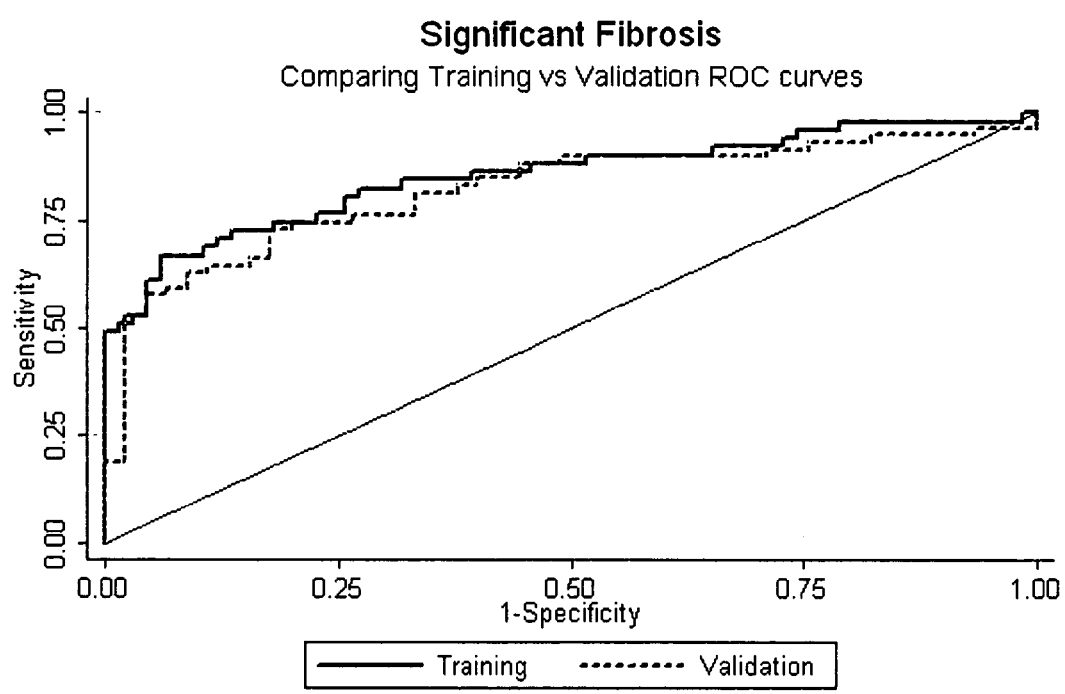
FIG. 1A-C: Receiver operating characteristic (ROC) curves of Hepascore for training and validation set for significant fibrosis, F2-F4, (FIG. 1A); advanced fibrosis, F3 and F4, (FIG. 1B); and cirrhosis, F4 (FIG. 1C). The AUC between the training and validation sets was not significantly different for significant fibrosis (P=0.6), advanced fibrosis (P=0.2) or cirrhosis (P=0.4).

Provided herein are methods of diagnosis of liver fibrosis and monitoring the progression or treatment of liver fibrosis in a patient comprising the steps of:

a) measuring the levels of four biochemical markers (i.e., α2-macroglobulin, γ-glutamyl transferase (GGT), bilirubin, and hyaluronic acid (HA)) in a sample from the patient, b) combining the values for each marker, age, and gender in an equation that gives a weight to each factor to determine an intermediate value, c) determining an end value or Hepascore using the intermediate value in a second equation, d) comparing the end value to a cut-off value in order to determine the presence or extent of liver fibrosis.

Samples

As used herein, the term "sample" refers to a biological specimen that may contain one or more markers such as α2MG, HA, bilirubin, or GGT. In particular aspects, serum is the sample. In other aspects, plasma is the sample. Plasma further containing anticoagulants or preservatives may be used provided the marker levels obtained therefrom are comparable to the marker levels obtained from serum.

One skilled in the art would understand that the levels of the four markers may be assayed in a single sample or may each be assayed from a separate sample, provided that the samples are obtained on the same day. The separate samples may be the same type of sample (e.g., serum) or may be of different types (e.g., serum and plasma). In a particular aspect, α2MG, HA, bilirubin, and GGT each are assayed in the same serum sample.

Determination of Marker Levels

α$_2$-Macroglobulin

The preferred method for determining α$_2$-macroglobulin (α2MG) levels is by nephelometry using the IMMAGE Immunochemistry System (Beckman Coulter). In this method, α2MG in the sample and an antibody against α2MG applied to the sample form α2MG-antibody aggregates. The IMMAGE system measures the rate of increase in light scattered from particles suspended in solution as a result of complexes formed during the above α2MG-antibody reaction. Reagents for this assay are provided with the IMMAGE system and the assay is run per the manufacturer's protocol. Briefly, reagents, calibrator (Beckman Calibrator 2), controls and samples are loaded into the system. The automated system adds 21 μL anti-α2MG antibody, 300 μL Buffer 1, and 20.42 μL Diluent-1 to 0.58 μL sample. The system calculates the level of α2MG in the sample and reports the result in g/L.

Other methods of determining α$_2$-macroglobulin levels may be used provided such methods provide a level comparable to that obtained by the preferred method. Such methods are well-known in the art and include, for example, immunoassays, including radioimmunoassay, enzyme-linked immunoassay (ELISA), and two-antibody sandwich assays may be used in invention methods. Monoclonal and polyclonal anti-α2MG antibodies useful in immunoassays can be readily obtained from a variety of sources.

Hyaluronic Acid

Hyaluronic acid (HA), also known as hyaluronate or hyaluronan, is a high molecular weight polysaccharide with an unbranched backbone comprised of dimeric units consisting of glucuronic acid and β-(1,3)-N-acetylglucosamine moieties connected by β-1,4 linkages. Hyaluronic acid can have a length of a few such dimeric units to more than 1,000, with each dimeric unit having a molecular weight of about 450 D. Hyaluronic acid is produced primarily by fibroblasts and other specialized connective tissue cells and plays a structural role in the connective tissue matrix. Hyaluronic acid is widely distributed throughout the body and can be found as a free molecule in, for example, plasma, synovial fluid, and urine.

Levels of HA are preferably determined using an enzyme-linked protein binding assay commercially available assay from Corgenix (Westminster, Colo.). This test is a sandwich protein binding assay which employs hyaluronic acid binding protein (HABP) as the capture molecule. In this assay, diluted serum or plasma and HA reference solutions are incubated in HABP-coated microwells. HA present in samples is captured by the immobilized binding protein (HABP). Unbound serum components are removed by washing, and HABP conjugated with horseradish peroxidase (HRP) solution is added to the microwells and complexes with bound HA. Unbound conjugated HABP is removed by washing and a chromogenic substrate of tetramethylbenzidine and hydrogen peroxide is added to develop a colored reaction. The intensity of the color is measured in optical density (O.D.) units with a spectrophotometer at 450 nm. Optical density is converted to HA concentration using a standard curve.

The procedure for the hyaluronic acid test from Corgenix is as follows. HA reference solutions and reagent blank are assayed in duplicate. Duplicate determinations are also recommended for patient samples. Reaction Buffer without serum is used for the reagent blank, which represents the 0 ng/mL HA reference solution. A water blank is included with each plate using 200 μL of reagent grade water, which is added at the completion of the assay, immediately prior to reading the plate. The water blank is to be used to zero the plate reader. Any microwell strips that will not be used in the run from the frame are removed and the foil pouch resealed. HA reference solutions and patient samples are prepared by adding 1 part of the solution or sample to 10 parts Reaction Buffer (blue solution). 100 µL of diluted HA reference solutions, patient samples, or reaction buffer (for reagent blank) is added to appropriate microwells. The well for the water blank is left empty. The plate is incubated for 60 minutes at room temperature. After the incubation is complete, the microwells are inverted to dump contents into a suitable container. Do not allow samples to contaminate other microwells. The wells are washed 4 times with working wash solution (PBS), filling wells completely. PBS in the water blank well will not interfere with the procedure. The microwells are inverted between each wash to empty fluid. Use a snapping motion of the wrist to shake the liquid from the wells. Pound and/or blot on absorbent paper to remove residual wash buffer. Do not allow wells to dry out between steps. 100 µL HRP-conjugated HABP Solution (red solution) is added to all wells except the water blank. The plate is incubated for 30 minutes at room temperature. After the incubation is complete, the microwells are carefully invert to dump conjugate solution and washed 4 times with PBS. Do not allow the wells to dry out. 100 µL One-component Substrate Solution is added to each well (except the water blank well) and the plate is incubated for 30 minutes at room temperature. Add substrate solution to wells at a steady rate. Blue color will develop in wells with positive samples. 100 µL Stopping Solution (0.36 N sulfuric acid) is added to each well (except the water blank well) to stop the enzymatic reaction. The stopping solution is added to the wells in the same order and at the same rate as the substrate solution. The stopping solution is not added to the water blank well, instead, 200 µL of reagent grade water is added to the water blank well. The plate reader is zeroed against the water blank well. The optical density (O.D.) of each well are read at 450 nm (650 nm reference). The O.D. of wells should be measured within one hour after the addition of stopping solution. The results are calculated as follows. The mean O.D. values of duplicate wells of HA reference solutions, reagent blanks and patient samples are calculated. The best fit curve using the mean O.D.s of the 0 ng/mL (reagent blank), 50, 100, 200, 500, and 500 ng/mL reference solutions is generated using either third order polynomial regression (recommended), linear regression or hand plotting. A new curve is plotted with each assay run. The HA concentrations (ng/mL) in patient samples can be determined from this curve.

Other methods of determining hyaluronic acid levels may be used provided such methods provide a level comparable to that obtained by the preferred method. Such methods are well-known in the art and include, for example, a variety of competitive and non-competitive binding assays and immunoassays. Competitive binding assays using $^{125}$I-labeled HA binding protein; competitive binding assays based on alkaline phosphatase labeled-hyaluronectin (HN); and non-competitive binding assays based on peroxidase-labeled proteoglycan or peroxidase-labeled HA-binding protein, among others, are well-known in the art. See, for example, Lindquist et al., Clin. Chem. 38:127-132 (1992); Delpech and Bertrand, Anal. Biochem. 149:555-565 (1985); Engstrom-Laurent et al., Scand. J. Clin. Lab. Invest. 45:497-504 (1985); Brandt et al., Acta Otolaryn. 442 (Suppl.):31-35 (1987); Goldberg, Anal. Biochem. 174:448-458 (1988); Chichibu et al., Clin. Chim. Acta 181:317-324 (1989); Li et al., Conn. Tissue Res. 19:243-254 (1989); Poole et al., Arth. Rheum. 33:790-799 (1990); Poole et al., J. Biol. Chem. 260:6020-6025 (1985); and Laurent and Tengblad, Anal. Biochem. 109:386-394 (1980)). A variety of immunoassay formats may be used to determine a level of HA, including radioimmunoassays and enzyme-linked immunoassays. Polyclonal or monoclonal anti-HA antibodies useful in immunoassays are commercially available from a variety of sources.

Bilirubin

Bilirubin is a chemical formed from the degradation of heme (a component of the hemoglobin present in red blood cells). Bilirubin in the blood is taken up by the liver, chemically modified in a process called conjugation, and secreted into the bile. The phrase "direct bilirubin" refers to conjugated bilirubin, whereas "indirect bilirubin" refers to unconjugated bilirubin. "Total bilirubin" refers to conjugated and unconjugated bilirubin.

Bilirubin levels are preferably determined from on fresh serum, within 36 hours of collection, using an automated biochemistry analyzer (Hitachi 917, Roche Diagnostics, Mannheim, Germany). In this method, total bilirubin, in the presence of a solubilizing agent, is coupled with a diazonium ion in a strongly acidic medium (pH 1-2) to form azobilirubin. The intensity of the color of the azobilirubin produced can be measured photometrically and is proportional to the total bilirubin in the sample. Samples, controls, and reagents are placed into the analyzer, the assay is run, and the results are automatically calculated. The results are reported in mg/dL, which can be converted to µmol/L by multiplying by a factor of 17.1.

Bilirubin levels can be assayed by other methods known in the art, provided such methods produce a level that is comparable to a level obtained using the preferred method. Such methods include, analyzing total bilirubin using diazotized sulfanilic acid reagent with blank correction (Malloy and Evelyn method; Abbott Laboratories and Ciba Corning). In another method, a sample is mixed with the reagent containing the detergent and the vanadate, at approximately pH 3, oxidizing the total bilirubin in the sample to biliverdin. The total bilirubin concentration in the sample can be obtained by measuring the absorbance before and after the vanadate oxidation (Total Bilirubin V assay; Wako Chemicals Inc., Richmond, Va.).

γ-Glutamyl Transferase

γ-glutamyl transferase (GGT), sometimes called γ-glutamyl transpeptidase (GGPT), is an enzyme that is compared with alkaline phosphatase (ALP) levels to distinguish between skeletal disease and liver disease. Because GGT is not increased in bone disorders, as is ALP, a normal GGT with an elevated ALP would indicate bone disease. Conversely, because the GGT is more specifically related to the liver, an elevated GGT with an elevated ALP would strengthen the diagnosis of liver or bile-duct disease.

GGT levels are preferably determined using an automated biochemistry analyzer such as Hitachi 917 biochemistry analyzer (Mannheim, Germany) with Roche Diagnostics reagents. In this method, GGT is measured in fresh serum within 36 hours of collection using this procedure. R1 reagent (123 mmol/L TRIS (i.e., tris(hydroxymethyl)-aminomethane) buffer, pH 8.25 (25° C.); 123 mmol/L glycylglycine; preservative; additive) is added to the sample. R2 reagent (10 mmol/L acetate buffer, pH 4.5 (25° C.); 25 mmol/L L-γ-glutamyl-3-carboxy-4-nitroanilide; stabilizer; preservative) is added to start the formation of L-γ-glutamyl-glycylglycine and 5-amino-2-nitrobenzoate from L-γ-glutamyl-3-carboxy-4-nitroanilide and glycylglycine in the presence of GGT. Gamma-glutamyltransferase transfers the γ-glutamyl group of L-γ-glutamyl-3-carboxy-4-nitroanilide to glycylglycine. The amount of 5-amino-2-nitrobenzoate liberated is proportional to the GGT activity and can be measured photometrically. Samples, controls, and reagents are placed into the analyzer, set up to run according to the manufacturer's protocol, the assay is run, and the results are automatically calculated. The results are reported in U/L, which can be converted to μkat/L by multiplying by a factor of 0.0167.

GGT levels can be determined by other methods known in the art provided such methods produce a result comparable to that obtained with the preferred method.

Determination of a Hepascore

Levels of the markers as determined above, along with age and gender, are input in the following equation to determine an intermediate value, y.

$$y=\exp(-4.185818-(0.0249*age)+(0.7464*gender)+(1.0039*\alpha2\text{-macroglobulin})+(0.0302*\text{hyaluronic acid})+(0.0691*\text{bilirubin})-(0.0012*GGT))$$

wherein, age is provided in years; male gender=1, female gender=0, $\alpha_2$-macroglobulin as reported in g/L; hyaluronate as reported in μg/L; bilirubin as reported in 1 mol/L; and GGT as reported in U/L.

The Hepascore, H, is calculated using the intermediate value, y, in the following equation:

$$H=y/(1+y)$$

Determination of Presence and Stage of Liver Fibrosis

The end value or Hepascore, H, is compared to a cut-off value, in order to identify significant fibrosis (METAVIR stages F2 to F4), cirrhosis (stage F4) or an absence of advanced fibrosis (stages F3 and F4).

Significant fibrosis (stages F2 to F4) can be distinguished from an absence of advanced fibrosis (F3 and F4). A Hepascore greater than or equal to a cut-off value of about 0.5 (preferably 0.5) is indicative of significant fibrosis, whereas, a Hepascore less than a cut-off value of about 0.5 (preferably 0.5) is indicative of an absence of advanced fibrosis. A Hepascore of greater than or equal to a cut-off value of about 0.84 (preferably 0.84) is indicative of cirrhosis, whereas a Hepascore of less than a cut-off value of about 0.84 (preferably 0.84) is indicative of the absence of cirrhosis.

Determination of Presence and Degree of Necroinflammatory Activity

The end value or Hepascore, H, is compared to a cut-off value, in order to distinguish no/mild necroinflammatory activity from moderate/severe necroinflammatory activity. A Hepascore greater than or equal to a cut-off value of about 0.5 (preferably 0.5) is indicative of moderate/severe necroinflammatory activity, whereas, a Hepascore less than about 0.5 (preferably 0.5) is indicative of no/mild necroinflammatory activity.

The following examples serve to illustrate the present invention. These examples are in no way intended to limit the scope of the invention.

Example 1

Selection of Patient Population

Patients were prospectively recruited from viral liver clinics in different tertiary referral centers; the training set was recruited from Sir Charles Gairdner Hospital (Perth, Australia) and the validation set from Westmead Hospital and Royal Prince Alfred Hospital (Sydney, Australia). All patients had detectable hepatitis C RNA at the time of evaluation and were treatment naive. Coexisting liver disease due to hepatitis B, haemochromatosis, alpha-1 antitrypsin deficiency, Wilson's disease, autoimmune and cholestatic liver diseases were excluded by standard clinical, laboratory, imaging and histological studies. No patient had human immunodeficiency virus co-infection or had undergone liver transplantation. Liver biopsy was performed as part of the routine clinical care of these patients. Age, gender and viral genotype were recorded at time of liver biopsy. Patients from the training set had the Fibrotest calculated.

The demographic and biochemical characteristics of the training (n=117) and validation sets (n=104) were generally similar (Table 1), but the validation set had a lower proportion of patients with genotype 1 (48% vs. 61%) and more genotype 4 patients (5% vs. 0%). There was also a trend towards a greater proportion of patients in the validation set having significant fibrosis (P=0.05) but not advanced fibrosis (P=0.4). The median portal tract number was 9 and the median biopsy length was 13 mm. The inter-observer agreement between pathologists was good (Kappa statistic, κ=0.56) for METAVIR staging and for significant fibrosis (Kappa statistic, κ=0.72).

TABLE 1

Clinical and laboratory features of the training and validation cohorts

| Variable | Tranining Set (n = 117) | Validation Set (n = 104) | P value |
|---|---|---|---|
| Age, years, mean (SD) | 40 (9) | 41 ± 9 | 0.5 |
| Female, n (%) | 38 (32%) | 28 (27%) | 0.4 |
| Genotype 1, n (%) | 67 (61%) | 50 (48%) | |
| Genotype 2/3, n (%) | 45 (39%) | 48 (47%) | |
| Genotype 4, n (%) | 0 | 5 (5%) | 0.03 |
| ALT, U/L | 124 ± 90 | 131 ± 99 | 0.5 |
| Bilirubin, μmol/L | 12 ± 8 | 12 ± 5 | 0.5 |
| Albumin, g/L | 42 ± 4 | 42 ± 3 | 0.7 |
| Stage F0, n (%) | 23 (19%) | 17 (16%) | |
| Stage F1, n (%) | 43 (37%) | 28 (27%) | |
| Stage F2, n (%) | 29 (25%) | 35 (34%) | |
| Stage F3, n (%) | 15 (13%) | 7 (7%) | |
| Stage F4, n (%) | 7 (6%) | 17 (16%) | 0.03 |
| Significant Fibrosis, F2 to F4, n (%) | 51 (44%) | 59 (57%) | 0.05 |
| Advanced Fibrosis, F3 and F4, n (%) | 22 (19%) | 24 (23%) | 0.4 |
| Grade A0, n (%) | 20 (17%) | 8 (8%) | 0.001 |
| Grade A1, n (%) | 75 (64%) | 63 (60%) | |
| Grade A2, n (%) | 13 (11%) | 32 (31%) | |
| Grade A3, n (%) | 9 (8%) | 1 (1%) | |
| Significant Activity, A2 and A3, n (%) | 22 (19%) | 33 (32%) | 0.03 |

Histology scored according to METAVIR. Genotype not available for five patients in the training set and one patient in the validation set.

Example 2

Assay of Markers

Training set sera were analyzed for 10 candidate markers. Bilirubin, ALT, GGT, and albumin were all measured on fresh serum within 36 hours of collection using an automated biochemistry analyzer (Hitachi 917, Roche Diagnostics, Mannheim, Germany). Other analyses were performed in batches using frozen serum stored at −20 C. TIMP-1 and MMP-2 were measured by enzyme-linked immunosorbent assay on a 96-well microplate (Biotrak, Amersham Biosciences, Bucks, UK). Hyaluronic acid was measured by an enzyme-linked protein binding assay, also on a 96-well microplate (Corgenix, Westminster, Colo., US). Alpha-2 macroglobulin, apolipoprotein-A1 and haptoglobin were all obtained by nephelometry (Image, Beckman Coulter, Brea, Calif., US). All analyses were performed at a central laboratory, PathCentre in Perth.

Univariate logistic regression analysis of the variables tested in the training set revealed age, gender, albumin, hyaluronic acid, α-2 macroglobulin and TIMP-1 to be associated with significant fibrosis (Table 2).

TABLE 2

Association of age, gender and biochemical serum markers with significant fibrosis in the training cohort (n = 117).

| Variable | Stage F0/F1 (n = 66) Mean | Stage F2-F4 (n = 51) Mean | P, univariate analysis |
|---|---|---|---|
| Age, years | 38.7 | 41.9 | 0.03 |
| Gender (female), % | 38.6% | 21.7% | 0.03 |
| ALT, U/L | 123.4 | 125.3 | 0.9 |
| GGT, U/L | 78.1 | 111.4 | 0.1 |
| Bilirubin, μmol/L | 10.8 | 13.0 | 0.2 |
| Albumin, g/L | 42.5 | 40.4 | <0.001 |
| Haptoglobin, g/lL | 1.0 | 0.9 | 0.4 |
| Hyaluronic Acid, μg/L | 20.7 | 107.3 | <0.001 |
| Apolipoprotein A1, g/L | 1.7 | 1.6 | 0.1 |
| α-2 macroglobulin, g/L | 2.3 | 3.3 | <0.001 |
| TIMP-1, ng/mL | 880 | 1404 | 0.002 |
| MMP-2, ng/mL | 731 | 830 | 0.1 |

Variables presented as n (%) or mean.

The final predictive model was computed from the results of the following four biochemical markers; bilirubin, GGT, alpha-2 macroglobulin and hyaluronic acid. The in-house analytical coefficients of variation were 1.7% at a bilirubin level of 16 μmol/L, 2.7% at a GGT activity of 33 U/L, 2.8% at an alpha-2 macroglobulin level of 2.5 g/L and 3.5% at a hyaluronic acid level of 50 μg/L.

Example 3

Analysis of Liver Biopsy

Liver biopsies of both training and validation sets were a minimum of 18 gauge with a minimum of five portal tracts and were routinely stained with hematoxylin-eosin and trichrome stains. Biopsies were interpreted according to the scoring schema developed by the METAVIR group by two expert liver pathologists who were masked to patient clinical characteristics and serum measurements. Thirty biopsies were scored by both pathologists and interobserver agreement was calculated using Kappa (κ) statistics. Fibrosis was scored on the 5-point METAVIR scale. Necro-inflammatory activity, based on assessment of piecemeal and lobular necrosis, was graded on a 4-point scale as follows: AO, no activity; A1, mild; A2, moderate; A3, severe.

Example 4

Statistical Analysis

Using the data from the training set, associations between each of the ten biochemical markers and the presence or absence of significant fibrosis were assessed by logistic regression. In addition, the diagnostic accuracy of each biochemical marker was assessed using receiver operating characteristic (ROC) curve analysis. All biochemical markers were combined with age and gender and entered into stepwise logistic regression analysis using a forward and a backward elimination procedure with a significance level of P=0.10. The dependent variable was defined as significant fibrosis as detected by liver biopsy. Biochemical markers with a high AUC or a high level of significance on univariate analysis were added to create different multivariable models. Models based on different marker combinations, were then compared using receiver operating characteristic (ROC) curves to determine which was most accurate in detecting significant fibrosis. A single model with the fewest variables and the greatest area under the curve (AUC) was selected and applied to the validation set. The logistic regression model consisted of:

$$y = \exp(-4.185818 - (0.0249*\text{age}) + (0.7464*\text{gender}) + (1.0039*\alpha_2\text{-macroglobulin}) + (0.0302*\text{hyaluronic acid}) + (0.0691*\text{bilirubin}) - (0.0012*\text{GGT}))$$

with age provided in years; male gender=1, female gender=0, $\alpha_2$-macroglobulin in g/L, hyaluronate in μg/L, bilirubin in μmol/L and GGT in U/L. The Hepascore, H, was calculated from the following equation:

$$H = y/(1+y).$$

Sensitivity, specificity, PPV and NPV for significant fibrosis, advanced fibrosis and cirrhosis were determined for various cut-off points between zero and one in the training set and validation set. The same Hepascore regression model was also used to calculate the accuracy for determining the combined endpoint of moderate to severe necroinflammatory activity (A2, A3) versus no or mild activity (A0, A1). Clinical and demographic characteristics between the training and validation sets were compared using the Student's t-test for continuous variables and chi squared test or Fisher exact test for categorical variables. A P value of less than 0.05 was considered significant. All statistical analysis was done using Stata version 8 (Stata Corp. 2003. Stata Statistical Software: Release 8.0. College Station, Tex.: Stata Corporation).

Example 5

Predictive Model

Figure 1B:
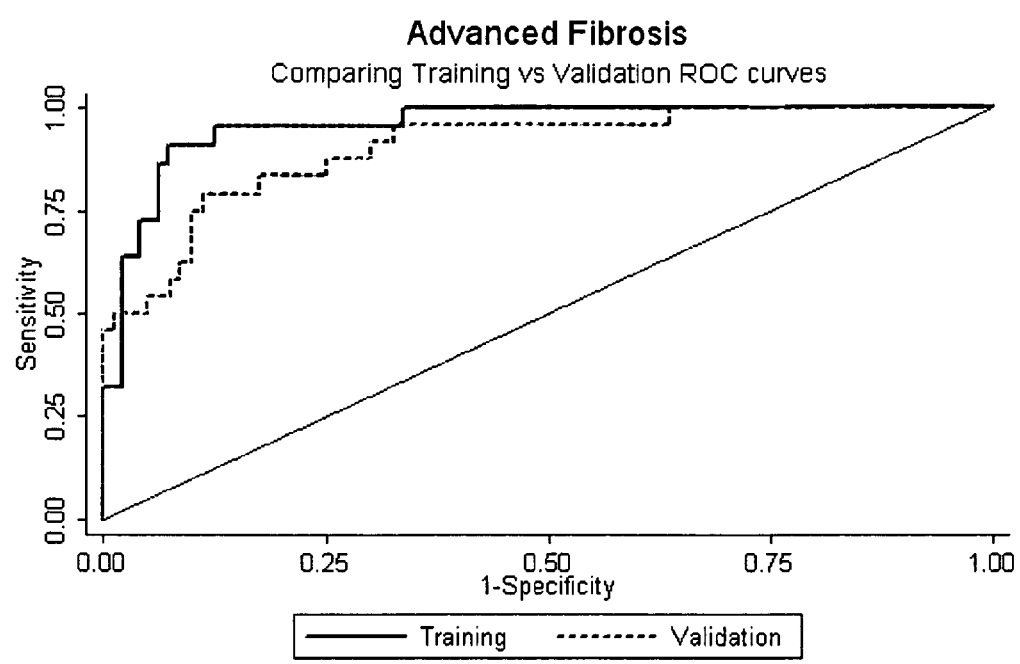
Figure 1C:
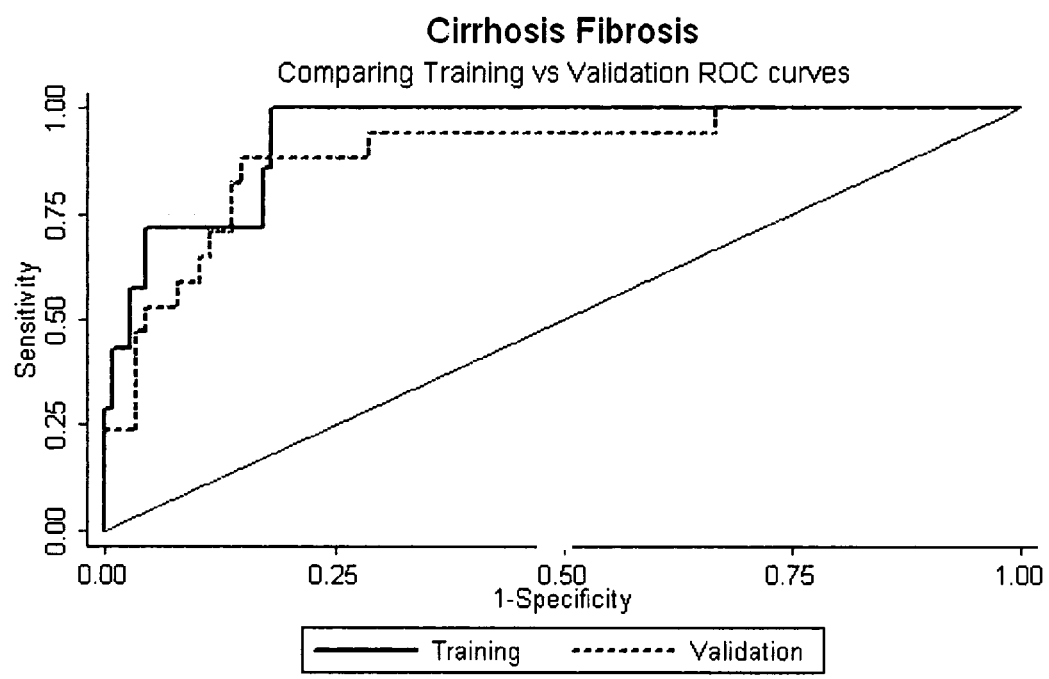

Biochemical markers assessed in the training set, were combined with age and gender in logistic regression analysis to create several models which were predictive of significant fibrosis. The optimal multivariable model was considered as having the largest AUC using ROC analysis. This model (Hepascore) consisted of age, gender, bilirubin, GGT, hyaluronic acid and α2 macroglobulin (Table 3) which provided a high AUC (95% confidence interval, CI) for the prediction of significant fibrosis (0.852 (95% CI, 0.778-0.926)), as well as for advanced fibrosis (0.957 (95% CI, 0.918-0.995)) and cirrhosis (0.938 (95% CI, 0.872-1.000)), as shown in FIG. 1. In comparison, the Fibrotest results in the training set provided AUC values for significant fibrosis, advanced fibrosis and cirrhosis of 0.793 (95% CI, 0.706-0.880), 0.906 (95% CI, 0.833-0.979) and 0.966 (95% CI, 0.918-1.000) respectively.

TABLE 3

Multiple logistic regression model for the prediction of significant fibrosis.

| Variable | Coefficient | SE | P | Odds ratio (95% CI) |
|---|---|---|---|---|
| Age, years | -0.02 | 0.03 | 0.44 | 0.98 (0.92-1.04) |
| Gender, female | 0.75 | 1.13 | 0.16 | 2.11 (0.74-6.05) |
| α-2 macroglobulin, g/L | 1.00 | 0.78 | 0.0001 | 2.73 (1.56-4.79) |
| Hyaluronic Acid, μg/L | 0.03 | 0.01 | 0.005 | 1.03 (1.01-1.05) |
| Bilirubin, μmol/L | 0.07 | 0.04 | 0.09 | 1.07 (0.99-1.16) |
| GGT, U/L | -0.01 | 0.01 | 0.59 | 1.00 (0.99-1.03) |

Figure 2:
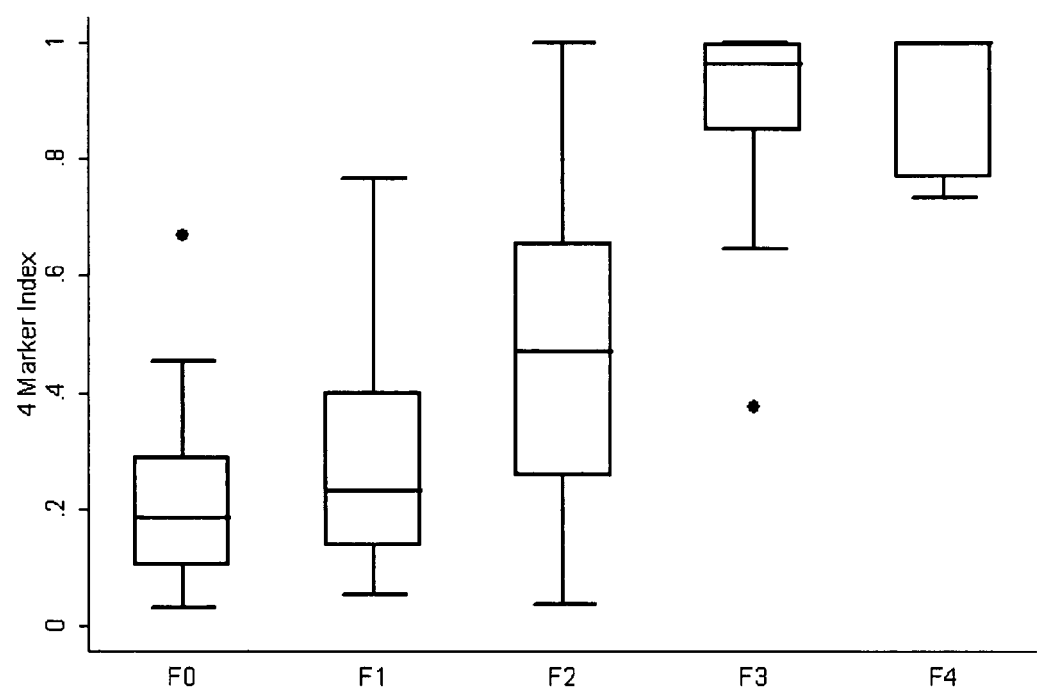
FIG. 2: Box plots of Hepascore according to fibrosis stage in the training set (n=117). Hepascore ranges from 0.0-1.0. Fibrosis staged according to METAVIR. Middle line represents median, inferior and superior ends of boxes represent $25^{th}$ and $75^{th}$ percentile respectively. Whiskers are $25^{th}$ and $75^{th}$ percentile±1.53*interquartile range. Dots represent outliers.

The Hepascore (range 0.0-1.0) increased significantly (P<0.001) as fibrosis stage increased (FIG. 2). A central cut-off point of 0.5 among the training set, predicted significant fibrosis (F2 to F4) with a sensitivity of 67% (95% C.I., 58.1-75.2) and a specificity of 92% (95% C.I., 87.6-97.2). Applying the same cut-off point of 0.5 for the prediction of advanced fibrosis (F3 and F4), sensitivity was 95% (95% C.I., 91.7-99.2) and specificity was 81% (95% C.I., 74.0-88.2). When a cut-off point of 0.84 was applied for detection of cirrhosis (F4), it provided a 71% (95% C.I., 63.2-79.6) sensitivity and an 84% (95% C.I., 76.9-90.3) specificity.

Example 6

Model Validation

The four-marker model, plus gender and age, was applied to the 104 patients in the validation set and provided AUCs of 0.820 (95% CI, 0.737-0.902) for significant fibrosis, 0.903 (95% CI, 0.835-0.971) for advanced fibrosis and 0.891 (95% CI, 0.805-0.976) for cirrhosis (FIG. 2).

Figure 3:
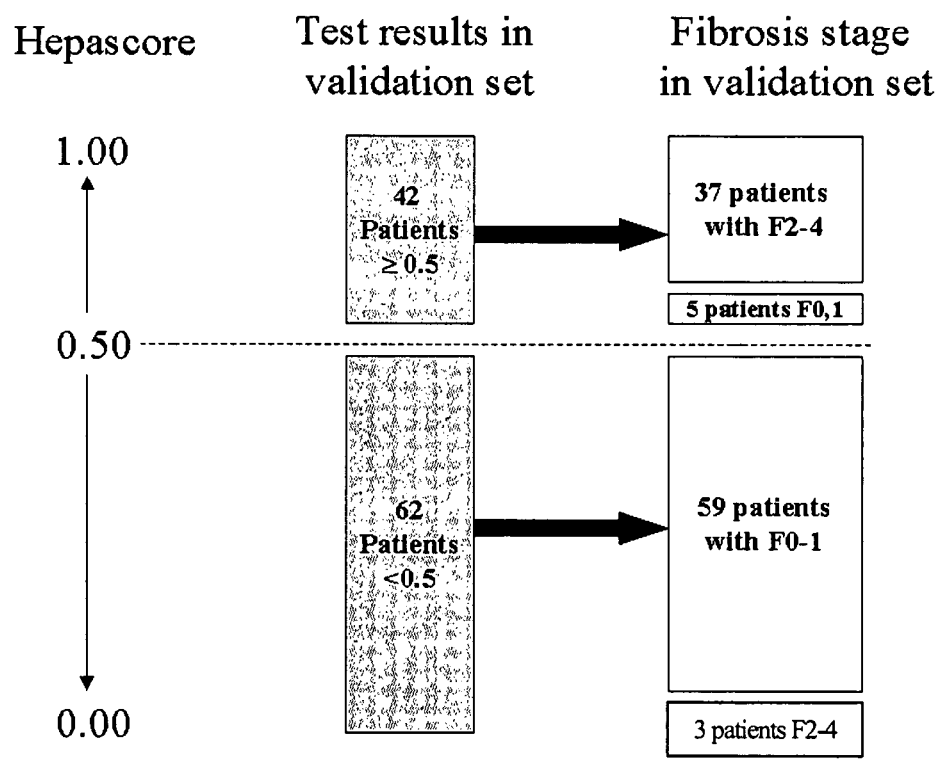
FIG. 3: Application of Hepascore Fibrosis Model to the Validation Set (n=104).

Among the validation cohort, 42 of 104 (40%) had a score≥0.5. A cut-off point of 0.5 gave a sensitivity of 63% (95% CI, 53.4%-72.0%) and a specificity of 89% (95% CI, 82.9%-94.9%) for the presence of significant fibrosis (F2 to F4). Therefore, 37 of 42 (88%) patients with a score of ≥0.5 had significant fibrosis (FIG. 3). A score of <0.5 was observed in the remaining 62 (60%) patients, which excluded advanced fibrosis (F3 and F4) with a sensitivity of 88% (95% CI, 81.1%-93.9%) and a specificity of 74% (95% CI, 65.3%-82.2%). A cut-off point of 0.84 yielded a sensitivity of 71% (95% CI, 61.8%-79.4%) and a specificity of 89% (95% CI, 82.4-94.6) for predicting cirrhosis (F4).

The Hepascore accurately predicted different levels of fibrosis among patients with chronic hepatitis C infection and its performance was confirmed in an independent validation set of patients from separate institutions. The Hepascore provided information for all patients; a score≥0.50 was 89-92% specific for the presence of significant fibrosis (METAVIR≥F2) and a score<0.50 was 88-95% sensitive for the absence of advanced fibrosis (METAVIR≥F3). Thus, in the two cohorts, a Hepascore≥0.50 provided high positive predictive values for the presence of significant fibrosis of 87% and 88%; a Hepascore<0.5 provided negative predictive values for advanced fibrosis of 95% and 98%; and a Hepascore<0.84 provided negative predictive values for cirrhosis of 94% and 98%.

The predictive value of a diagnostic test varies according to the underlying prevalence of the disease or symptom. Therefore, as treatment is generally recommended when significant fibrosis is present (Hepatology 39: 1147-71 (2004)), patients with a Hepascore≥0.50 may be considered for anti-viral therapy without the requirement for liver biopsy. In addition, the exclusion of advanced fibrosis among patients who have a Hepascore<0.5 may be particularly useful in providing prognostic information for patients who are reluctant to undergo biopsy or among elderly patients who are unlikely to develop liver related morbidity or mortality in the absence of advanced fibrosis (Lancet 349: 825-32 (1997)). Finally, a score>0.84 is 84%-89% specific for the presence of cirrhosis. This may be useful to avoid liver biopsy in patients in whom occult cirrhosis is suspected or to guide management decisions regarding variceal and cancer screening and patient follow-up (Gut 49:11-21 (2001)).

The Hepascore model was accurate in excluding moderate to severe necroinflammatory activity (A2 and A3), providing an AUC of 0.707 (95% CI, 0.579-0.835) in the training set, with 59% (95% CI, 50.2%-68.0%) sensitivity and 73% (95% CI, 64.6%-80.7%) specificity.

Example 7

Prediction of Fibrosis in Patients with Non-Alcoholic/Alcoholic Fatty Liver Disease In this study, Hepascore was used for the prediction of liver fibrosis in patients with non-alcoholic/alcoholic fatty liver disease (NAFLD/AFLD). Thirteen patients clinically suspected of having NAFLD/AFLD had liver biopsies, which were graded according to NAFLD activity score using the scoring system reported by Kleiner et al. (Hepatology 2005; 41: 1313). Serum samples were analysed for hyaluronic acid, alpha2 macroglobulin, gamma glutamyl transpeptidase and bilirubin. The intermediate value for each patient was calculated as follows:

$$y = \exp(-4.185818 - (0.0249*age) + (0.7464*gender) + (1.0039*\alpha_2\text{-macroglobulin}) + (0.0302*\text{hyaluronic acid}) + (0.0691*\text{bilirubin}) - (0.0012*GGT))$$

with age provided in years; male gender=1, female gender=0, $\alpha_2$-macroglobulin in g/L, hyaluronate in µg/L, bilirubin in µmol/L and GGT in U/L. The Hepascore, H, for each patient was calculated from the following equation:

$$H = y/(1+y).$$

The Hepascore was used to predict liver fibrosis in these patients, wherein a Hepascore greater than or equal to a cut-off value of 0.5 is indicative of significant fibrosis, and whereas a Hepascore of less than 0.5 is indicative of an absence of advanced fibrosis. A Hepascore of greater than or equal to a cut-off value of 0.84 is indicative of cirrhosis, whereas a Hepascore of less than a cut-off value of 0.84 is indicative of the absence of cirrhosis. Case notes were reviewed for the following metabolic syndrome risk factors: diabetes, elevated body mass index (BMI), hyperlipidaemia and hypertension. Alcohol consumption was assessed as standard drinks per week. Liver fibrosis of biopsy samples was graded using METAVIR score from F0 to F4 with a grade of F2, F3 or F4 defined as significant fibrosis.

Ten patients had significant fibrosis on liver biopsy (i.e., a METAVIR score of F2-F4) of which three patients had cirrhosis (i.e., a METAVIR score of F4). Six patients had significant steatosis (greater than 50% steatosis). Eight patients were overweight, having a BMI above 25. Two patients had diabetes, five were hyperlipidaemic, and four were hypertensive. One patient with morbid obesity had all three risk factors and one patient had two risk factors (diabetes and hypertension). Six patients had only one risk factor. Stated alcohol consumption was less than five standard drinks per week in nine patients, the remaining four patients consumed more than 21 drinks per week.

Calculation of Hepascore predicted ten patients with significant fibrosis and three with insignificant fibrosis. One patient had a discrepant result: a biopsy grade of F1 compared to a predicted grade of F2, F3 or F4. Thus, Hepascore correctly categorized the presence or absence of significant fibrosis in 12 of 13 patients with non-alcoholic/alcoholic fatty liver disease.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method of diagnosing liver fibrosis in a patient, said method comprising:
   a) assaying the concentration of markers in a sample from said patient, wherein said markers are α2-macroglobulin, γ-glutamyl transferase (GGT), bilirubin, and hyaluronic acid;
   b) determining, with a suitably programmed computer, an end value, H, using an algorithm, wherein said algorithm is, $H=y/(1+y)$ wherein, $y=\exp(-X-(C_1*\text{age})+(C_2*\text{gender})+(C_3*\alpha2\text{-macroglobulin})+(C_4*\text{hyaluronic acid})+(C_5*\text{bilirubin})-(C_6*\text{GGT}))$ wherein,
   X is between −6.8460 and −1.5257 inclusive,
   $C_1$ is between −0.0877 and 0.0378 inclusive,
   $C_2$ is between 0.3064 and 1.7992 inclusive,
   $C_3$ is between 0.4406 and 1.5672 inclusive,
   $C_4$ is between 0.0090 and 0.0515 inclusive,
   $C_5$ is between −0.0099 and 0.1482 inclusive,
   $C_6$ is between −0.0055 and 0.0032 inclusive, and
   wherein,
   age is in years,
   male gender=1, female gender=0,
   $\alpha_2$-macroglobulin is in g/L,
   hyaluronic acid is in µg/L,
   bilirubin is in µmol/L,
   GGT is in U/L; and
   c) comparing said end value, H, to a cut-off value associated with the presence of liver fibrosis and diagnosing said patient with liver fibrosis when the end value is greater than or equal to the cut-off value.

2. The method of claim 1, wherein $y=\exp(-4.185818-(0.0249*\text{age})+(0.7464*\text{gender})+(1.0039*\alpha_2\text{-macroglobulin})+(0.0302*\text{hyaluronic acid})+(0.0691*\text{bilirubin})-(0.0012*\text{GGT}))$.

3. The method of claim 1, wherein said cut-off value is 0.5, and wherein an end value, H, of greater than or equal to 0.5 is indicative of significant fibrosis or an end value, H, of less than 0.5 is indicative of the absence of advanced fibrosis.

4. The method of claim 1, wherein said cut-off value is 0.84 and an end value, H, less than 0.84 is indicative of the absence of cirrhosis of the liver.

5. The method of claim 1, wherein said cut-off value is 0.84 and an end value, H, greater than or equal to 0.84 is indicative of the presence of cirrhosis.

6. The method of claim 1, wherein said sample is serum.

7. The method of claim 1, wherein said sample is plasma.

8. The method of claim 1, wherein said end value is used for the choice of a suitable treatment for the patient.

9. A method of monitoring progression of liver fibrosis in a patient, said method comprising:
   a) obtaining a first sample from said patient;
   b) assaying the concentration of markers in a sample from said patient, wherein said markers are α2-macroglobulin, γ-glutamyl transferase (GGT), bilirubin, and hyaluronic acid;
   c) determining, with a suitably programmed computer, an end value, H, using an algorithm, wherein said algorithm is, $H=y/(1+y)$ wherein, $y=\exp(-X-(C_1*\text{age})+(C_2*\text{gender})+(C_3*\alpha2\text{-macroglobulin})+(C_4*\text{hyaluronic acid})+(C_5*\text{bilirubin})-(C_6*\text{GGT}))$ wherein,
   X is between −6.8460 and −1.5257 inclusive,
   $C_1$ is between −0.0877 and 0.0378 inclusive,
   $C_2$ is between 0.3064 and 1.7992 inclusive,
   $C_3$ is between 0.4406 and 1.5672 inclusive,
   $C_4$ is between 0.0090 and 0.0515 inclusive,
   $C_5$ is between −0.0099 and 0.1482 inclusive,
   $C_6$ is between −0.0055 and 0.0032 inclusive, and
   wherein,
   age is in years,
   male gender=1, female gender=0,
   $\alpha_2$-macroglobulin is in g/L,
   hyaluronic acid is in µg/L,
   bilirubin is in µmol/L,
   GGT is in U/L; and
   d) comparing said end value, H, to a cut-off value associated with the presence of liver fibrosis, and determining the extent of liver fibrosis in said patient when the end value is greater than or equal to the cut-off value;
   e) obtaining a second sample from said patient, wherein said second sample is obtained after said first sample;
   f) repeating steps b)-d) to determine the extent of liver fibrosis as indicated by said second sample; and
   g) determining progression of liver fibrosis by comparing the extent of liver fibrosis indicated by said first sample to the extent of liver fibrosis indicated by said second sample;

wherein a higher extent in liver fibrosis as indicated by the second sample in comparison to the first sample indicates progression in liver fibrosis or a lesser extent in liver fibrosis as indicated by the second sample in comparison to the first sample indicates a regression in liver fibrosis.

10. The method of claim 9, wherein $$y=\exp(-4.185818-(0.0249*age)+(0.7464*gender)+(1.0039*\alpha_2\text{-macroglobulin})+(0.0302*\text{hyaluronic acid})+(0.0691*\text{bilirubin})-(0.0012*GGT)).$$

11. The method of claim 9, wherein said cut-off value is 0.5, and wherein an end value, H, of greater than or equal to said cut-off value is indicative of significant fibrosis or an end value, H, of less than said cut-off value is indicative of the absence of advanced fibrosis.

12. The method of claim 9, wherein said cut-off value is 0.84 and an end value, H, of less than 0.84 is indicative of an absence of cirrhosis of the liver.

13. The method of claim 9, wherein said cut-off value is 0.84 and an end value, H, greater than or equal to 0.84 is indicative of the presence of cirrhosis of the liver.

14. The method of claim 9, wherein said sample is serum.

15. The method of claim 9, wherein said sample is plasma.

16. A method of monitoring the efficacy of liver fibrosis therapy in a patient in need thereof, said method comprising:
   a) obtaining a first sample from said patient;
   b) assaying the concentration of markers in a sample from said patient, wherein said markers are $\alpha$2-macroglobulin, $\gamma$-glutamyl transferase (GGT), bilirubin, and hyaluronic acid;
   c) determining, with a suitably programmed computer, an end value, H, using an algorithm, wherein said algorithm is, $$H=y/(1+y)$$

wherein, $$y=\exp(-X-(C_1*age)+(C_2*gender)+(C_3*\alpha2\text{-macroglobulin})+(C_4*\text{hyaluronic acid})+(C_5*\text{bilirubin})-(C_6*GGT))$$

wherein,
      X is between −6.8460 and −1.5257 inclusive,
      $C_1$ is between −0.0877 and 0.0378 inclusive,
      $C_2$ is between 0.3064 and 1.7992 inclusive,
      $C_3$ is between 0.4406 and 1.5672 inclusive,
      $C_4$ is between 0.0090 and 0.0515 inclusive,
      $C_5$ is between −0.0099 and 0.1482 inclusive,
      $C_6$ is between −0.0055 and 0.0032 inclusive, and
   wherein,
      age is in years,
      male gender=1, female gender=0,
      $\alpha_2$-macroglobulin is in g/L,
      hyaluronic acid is in µg/L,
      bilirubin is in µmol/L,
      GGT is in U/L; and
   d) comparing said end value, H, to a cut-off value associated with the presence of liver fibrosis, and determining the extent of liver fibrosis in said patient when the end value is greater than or equal to the cut-off value;
   e) obtaining a second sample from said patient, wherein said second sample is obtained after said first sample;
   f) repeating steps b)-d) to determine the extent of liver fibrosis as indicated by said second sample; and
   g) determining the efficacy of the liver fibrosis therapy by comparing the extent of liver fibrosis indicated by said first sample to the extent of liver fibrosis indicated by said second sample; wherein an equivalent or higher extent in liver fibrosis as indicated by the second sample in comparison to the first sample indicates the liver fibrosis therapy is not efficacious in treating liver fibrosis, or a lesser extent in liver fibrosis as indicated by the second sample in comparison to the first sample indicates the liver fibrosis therapy is efficacious in treating liver fibrosis.

17. The method of claim 16, wherein $$y=\exp(-4.185818-(0.0249*age)+(0.7464*gender)+(1.0039*\alpha_2\text{-macroglobulin})+(0.0302*\text{hyaluronic acid})+(0.0691*\text{bilirubin})-(0.0012*GGT)).$$

18. The method of claim 16, further comprising predicting said patient has significant or advanced fibrosis when said determined end value, H, is greater than a cut-off value of 0.5, or predicting said patient does not have advanced fibrosis when said determined end value, H, is lower than a cut-off value of 0.5.

19. The method of claim 16, wherein said cut-off value is 0.84 and an end value, H, of less than 0.84 is indicative of an absence of cirrhosis of the liver.

20. The method of claim 16, wherein said cut-off value is 0.84 and an end value, H, greater than or equal to 0.84 is indicative of the presence of cirrhosis of the liver.

21. The method of claim 16, wherein said sample is serum.

22. The method of claim 16, wherein said sample is plasma.

23. A method of predicting hepatic necroinflammatory activity in a patient, said method comprising:
   a) assaying the concentration of markers in a sample from said patient, wherein said markers are $\alpha$2-macroglobulin, $\gamma$-glutamyl transferase (GGT), bilirubin, and hyaluronic acid;
   b) determining, with a suitably programmed computer, an end value, H, using an algorithm, wherein said algorithm is, $$H=y/(1+y)$$

wherein, $$y=\exp(-X-(C_1*age)+(C_2*gender)+(C_3*\alpha2\text{-macroglobulin})+(C_4*\text{hyaluronic acid})+(C_5*\text{bilirubin})-(C_6*GGT))$$

wherein,
      X is between −6.8460 and −1.5257 inclusive,
      $C_1$ is between −0.0877 and 0.0378 inclusive,
      $C_2$ is between 0.3064 and 1.7992 inclusive,
      $C_3$ is between 0.4406 and 1.5672 inclusive,
      $C_4$ is between 0.0090 and 0.0515 inclusive,
      $C_5$ is between −0.0099 and 0.1482 inclusive,
      $C_6$ is between −0.0055 and 0.0032 inclusive, and
   wherein,
      age is in years,
      male gender=1, female gender=0,
      $\alpha_2$-macroglobulin is in g/L,
      hyaluronic acid is in µg/L,
      bilirubin is in µmol/L,
      GGT is in U/L; and
   c) comparing said end value, H, to a cut-off value associated with the presence of necroinflammatory activity and predicting said patient with necroinflammatory activity when the end value is greater than or equal to the cut-off value.

24. The method of claim 23, wherein $$y=\exp(-4.185818-(0.0249*age)+(0.7464*gender)+(1.0039*\alpha_2\text{-macroglobulin})+(0.0302*\text{hyaluronic acid})+(0.0691*\text{bilirubin})-(0.0012*GGT)).$$

25. The method of claim 23, further comprising predicting said patient has moderate to severe necroinflammatory activity when said determined end value, H, is greater than a cut-off value of 0.5, or predicting said patient has mild or no necroinflammatory activity when said determined end value, H, is lower than a cut-off value of 0.5.

26. The method of claim 23, wherein said sample is serum.

27. The method of claim 23, wherein said sample is plasma.

28. A system for predicting the presence of liver fibrosis in an individual, said system comprising,
   (a) an input device for entry of data comprising $\alpha_2$-macroglobulin, hyaluronic acid, bilirubin, and $\gamma$-glutamyl transferase levels as determined from a sample from said individual and data for age and gender;
   (b) a processor connected to said input device, said processor having software for:
   1) computing an end value, H, using an algorithm, wherein said algorithm is, $$H = y/(1+y)$$

wherein, $$y = \exp(-X - (C_1 * \text{age}) + (C_2 * \text{gender}) + (C_3 * \alpha2\text{-macroglobulin}) + (C_4 * \text{hyaluronic acid}) + (C_5 * \text{bilirubin}) - (C_6 * \text{GGT}))$$

wherein,
   X is between −6.8460 and −1.5257 inclusive,
   $C_1$ is between −0.0877 and 0.0378 inclusive,
   $C_2$ is between 0.3064 and 1.7992 inclusive,
   $C_3$ is between 0.4406 and 1.5672 inclusive,
   $C_4$ is between 0.0090 and 0.0515 inclusive,
   $C_5$ is between −0.0099 and 0.1482 inclusive,
   $C_6$ is between −0.0055 and 0.0032 inclusive, and wherein,
   age is in years,
   male gender=1, female gender=0,
   $\alpha_2$-macroglobulin is in g/L,
   hyaluronic acid is in µg/L,
   bilirubin is in µmol/L,
   GGT is in U/L; and
   2) comparing said end value to a cut-off value associated with the presence of liver fibrosis and predicting said patient with liver fibrosis when the end value is greater than or equal to the cut-off value,
   (c) a data output device for outputting the result generated by said processor.

29. The method of claim 28, wherein $$y = \exp(-4.185818 - (0.0249 * \text{age}) + (0.7464 * \text{gender}) + (1.0039 * \alpha_2\text{-macroglobulin}) + (0.0302 * \text{hyaluronic acid}) + (0.0691 * \text{bilirubin}) - (0.0012 * \text{GGT})).$$

30. The method of claim 28, further comprising predicting said patient has significant or advanced fibrosis when said determined end value, H, is greater than a cut-off value of 0.5, or predicting said patient does not have advanced fibrosis when said determined end value, H, is lower than a cut-off value of 0.5.

31. The system of claim 28, wherein said cut-off value is 0.84 and an end value, H, of less than 0.84 is indicative of an absence of cirrhosis of the liver.

32. The system of claim 28, wherein said cut-off value is 0.84 and an end value, H, greater than or equal to 0.84 is indicative of the presence of cirrhosis of the liver.

33. The system of claim 28, wherein said input device is a keyboard or a cable in data communication with a computer, a network, a server, or an analytical instrument.

34. The system of claim 28, wherein said output device is selected from the group consisting of a video display monitor, a printer.

* * * * *